(12) United States Patent
Farra et al.

(10) Patent No.: US 8,933,035 B2
(45) Date of Patent: Jan. 13, 2015

(54) TRANSGLUTAMINASE-ACTIVATING PEPTIDE AND COSMETIC OR PHARMACEUTICAL COMPOSITION CONTAINING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 220 days.

(21) Appl. No.: 13/394,043

(22) PCT Filed: Aug. 31, 2010

(86) PCT No.: PCT/FR2010/000595
§ 371 (c)(1), (2), (4) Date: Mar. 21, 2012

(87) PCT Pub. No.: WO2011/027048
PCT Pub. Date: Mar. 10, 2011

(65) Prior Publication Data
US 2012/0172309 A1    Jul. 5, 2012

(30) Foreign Application Priority Data

Sep. 4, 2009  (FR) ...................................... 09 04218

(51) Int. Cl.
| | | |
|---|---|---|
| *A61K 38/08* | (2006.01) | |
| *C07K 7/06* | (2006.01) | |
| *C07K 5/11* | (2006.01) | |
| *A61K 8/64* | (2006.01) | |
| *A61Q 19/00* | (2006.01) | |
| *A61Q 19/08* | (2006.01) | |
| *A61K 38/00* | (2006.01) | |

(52) U.S. Cl.
CPC .................. *C07K 5/1019* (2013.01); *A61K 8/64* (2013.01); *A61Q 19/00* (2013.01); *A61Q 19/08* (2013.01); *C07K 7/06* (2013.01); *A61K 38/00* (2013.01)
USPC ........ 514/18.6; 514/21.7; 514/21.8; 530/328; 530/329; 530/330

(58) Field of Classification Search
CPC ......... A61K 38/00; A61K 38/03; C07K 7/00; A61Q 19/00; A61Q 19/002; A61Q 19/004; A61Q 19/08
See application file for complete search history.

(56) References Cited

U.S. PATENT DOCUMENTS

| | | | |
|---|---|---|---|
| 6,887,473 B1 * | 5/2005 | Brooks et al. ............. | 424/152.1 |
| 2002/0076834 A1 | 6/2002 | Detlef et al. | |
| 2003/0162706 A1 * | 8/2003 | Peters et al. .................... | 514/12 |
| 2006/0149034 A1 | 7/2006 | Edelberg et al. | |
| 2007/0134172 A1 | 6/2007 | Buchholz et al. | |

FOREIGN PATENT DOCUMENTS

| | | | |
|---|---|---|---|
| JP | 2004-115451 | 4/2004 | |
| WO | 97/02340 | 1/1997 | |
| WO | WO 97/02340 | * 1/1997 | ............... C12N 9/10 |
| WO | 97/47314 | 12/1997 | |
| WO | 2005/054222 | 6/2005 | |
| WO | WO2007055578 A1 | * 5/2007 | |

OTHER PUBLICATIONS

Transglutaminase [*Homo sapien*], GenBank: AAB95430.1; pp. 1-2, 1998, obtained from http://www.ncbi.nlm.nih.gov/protein/aab95430 on Apr. 16, 2014.*
Transglutaminase [*Homo sapien*], GenBank: AAA36739.1; pp. 1-2, 1993, obtained from http://www.ncbi.nlm.nih.gov/protein/aaa36739 on Apr. 16, 2014.*
protein-glutamine gamma-glutamyltransferase 2 isoform a [*Homo sapiens*], NCBI Reference Sequence: NP_004604.2; pp. 1-4, 2014 obtained from http://www.ncbi.nlm.nih.gov/protein/np_004604 on Apr. 16, 2014.*
Transglutaminase [*Homo sapien*], GenBank:AAA61156.1, pp. 1-2, 1995, obtained from http://www.ncbi.nlm.nih.gov/protein/aaa61156 on Apr. 16, 2014.*
PCT, International Search Report, International Application No. PCT/FR2010/000595 (mailed Jan. 17, 2011, published Mar. 10, 2011).
Hitomi, K., "Transglutaminases in skin epidermis," *Eur. J. Dermatol.*, vol. 15, No. 5, pp. 313-319 (Sep.-Oct. 2005).
Ghadially, R. et al., "The Aged Epidermal Permeability Barrier," *The Journal of Clinical Investigation*, vol. 95, pp. 2281-2290 (May 1995).
Huber, M. et al., "Mutations of Keratinocyte Transglutaminase in Lemellar Ichthyosis," *Science*, vol. 267, pp. 525-528 (Jan. 1995).
Kullmann, W., "Proteases as Catalysts for Enzymic Syntheses of Opioid Peptides," *The Journal of Biological Chemistry*, vol. 255, No. 17, pp. 8234-8238 (Sep. 10, 1980).
Lorand, L. et al., "Transglutaminases: Crosslinking Enzymes with Pleiotropic Functions," *Nature Reviews*, Molecular Cell Biology, vol. 4, pp. 140-156 (Feb. 2003).
Matsuki, M. et al., "Defective stratum corneum and early neonatal death in mice lacking the gene for transglutaminase 1 (keratinocyte transglutaminase)," *Proc. Natl. Acad. Sci., USA*, vol. 95, pp. 1044-1049 (Feb. 1998).
Webster's Ninth New Collegiate Dictionary, 1988, pp. 933, 946 defining "prevent" and "protect".

* cited by examiner

*Primary Examiner* — Karlheinz R Skowronek
*Assistant Examiner* — Lianko Garyu
(74) *Attorney, Agent, or Firm* — Thompson Hine L.L.P.

(57) ABSTRACT

A peptide of general formula (I):

$$R_1\text{-}(AA)_n\text{-}X_1\text{-}X_2\text{-}Arg\text{-}Arg\text{-}Gly\text{-}X_3\text{-}X_4\text{-}(AA)_p\text{-}R_2, \text{ and}$$

cosmetic and pharmaceutical compositions are disclosed that include at least one peptide of general formula (I), in a physiologically suitable medium. Also disclosed are methods for activating human transglutaminase to reinforce the skin barrier function and to stimulate epidermal regeneration and differentiation or for cosmetic treatment to treat signs of skin ageing, which include administering a composition containing the peptide of general formula (I) as an active ingredient.

9 Claims, 1 Drawing Sheet

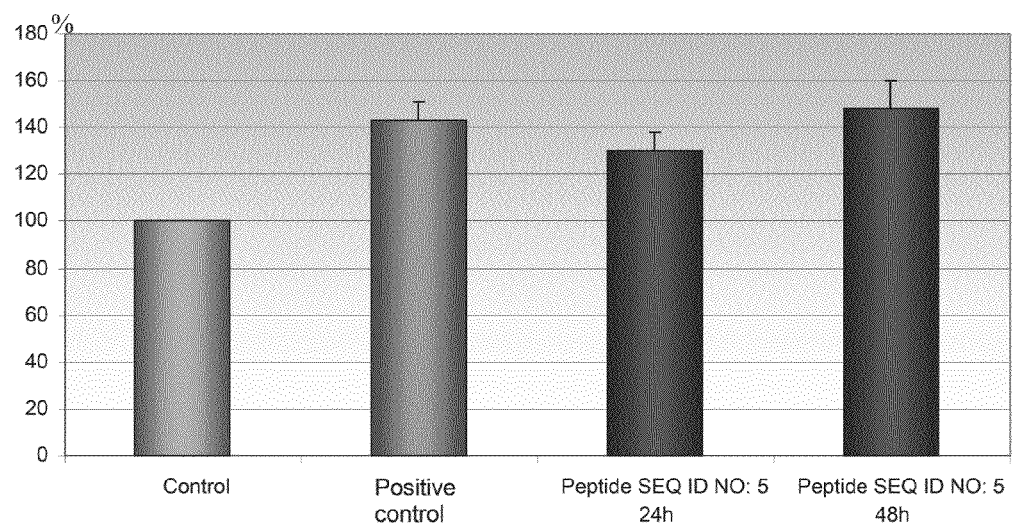

TRANSGLUTAMINASE-ACTIVATING PEPTIDE AND COSMETIC OR PHARMACEUTICAL COMPOSITION CONTAINING SAME

The present invention is concerned with the cosmetic and pharmaceutical field, more specifically the field of dermatology. The present invention relates to peptides of general formula (I):

$$R_1\text{-}(AA)_n\text{-}X_1\text{-}X_2\text{-}Arg\text{-}Arg\text{-}Gly\text{-}X_3\text{-}X_4\text{-}(AA)_p\text{-}R_2.$$

The present invention also relates to a cosmetic or pharmaceutical composition containing a peptide of general formula (I), used alone or in combination with at least one other active ingredient, in a physiologically suitable medium. The invention also relates to the use of this new peptide as an active ingredient which activates human transglutaminase.

The invention also relates to the use of this new peptide as an active ingredient in a cosmetic composition to reinforce the skin barrier function and to stimulate epidermal regeneration and differentiation.

The invention also relates to the use of this new peptide as a pharmaceutical composition.

The invention also relates to a cosmetic treatment method for preventing and/or for protecting the skin and the skin appendages against external stresses, and for combatting the signs of skin ageing, in accordance with which an effective amount of active ingredient or of a composition containing said active ingredient is applied to the areas to be treated.

The primary function of the epidermis is to form a barrier between the external environment and the internal medium. It is the outermost layer of the epidermis, the stratum corneum, which ensures this function. It is formed of keratinocytes in the final stage of their differentiation, that is to say corneocytes, which are bonded to one another by an intercellular cement which is both flexible and impermeable. In the stratum corneum, a distinction is thus made between a cellular compartment formed of corneocytes and an extracellular compartment formed primarily of lipids organised in multi-lamellar structures. The corneocytes are surrounded by a specific membrane, called a cornified envelope, which is largely responsible for the strength, insolubility and suppleness of the skin. The cornified envelope is formed of a mixture of structural proteins interconnected by covalent bonds under the action of transglutaminase. The main proteins forming the cornified envelope are envoplakin, periplakin, involucrin, small proline-rich proteins (SPR proteins) and loricrin.

Transglutaminases (EC 2.3.2.13) are a family of calcium-dependent enzymes which catalyse the formation of peptide bridges between an ε-amino of a lysine residue and a γ-carboxamide of a glutamine residue, these extra and intramolecular bridges being extremely resistant to degradation (Lorand et al., Nat Rev Mol Cell Biol. February; 4(2), 2003). In humans, nine transglutaminases have been identified, four of which are expressed in the skin.

Transglutaminase-1 (TG1) is expressed in keratinocytes and is present in a form bonded to the membrane.

Transglutaminase-2 (TG2, type 2a or 2b) is only present in the bottom layer of the epidermis. It is soluble and does not appear to play a role in the formation of the cornified envelope. TG2 has the ability to form covalent bonds between proteins, but can also bond GTP or GDP, and can thus behave similarly to a G protein, in particular if the cell is experiencing apoptosis or necrosis. TG2 can also be exported to the membrane and can combine with integrins to increase cellular adhesion, cell distribution and cell migration over the fibronectin of the extracellular matrix. Apart from its pleiotropic functions, TG2 is also involved in healing inter alia.

Transglutaminase-3 (TG3) is expressed in the pilose follicles and in the latter stages of keratinocyte differentiation.

Transglutaminase-5 (TG5) is present in the upper layers of the epidermis and also plays a role in the first stages of epidermal differentiation.

In the epidermis, TG1, TG3 and TG5 are involved in the formation of the cornified envelope (Lorand et al., Nat Rev Mol Cell Biol. February; 4(2), 2003).

TGs have rather diverse substrates. They are therefore able to cross-link keratins to one another and to filaggrin, which stabilises and coordinates the keratin-filaggrin network in the cornified cells.

During the first stages of epidermal differentiation, TGs improve the anchoring of desmosomes, then in the granular layer these same TGs ensure the attachment of certain lipids to the cornified envelope and the bonding of loricrin to the small proline rich proteins (SPRs). In the upper granular layers, the lipids originating from golgi bodies are cross-linked by TG1 and TG5 to the precursor proteins of the envelope, which are already cross-linked in part. Lastly, the phase of desquamation, which takes place at the outermost cornified layers, involves additional cross-linkings of loricrin and other proteins, which involves TG1.

A number of studies have shown that the three TGs involved in the formation of the cornified envelope in the epidermis have different functions (Candi et al 1995).

The key role of transglutaminases in the formation of the stratum corneum, mostly in epidermal differentiation and as a consequence of their barrier function, has been confirmed by specific pathological models. TG1−/− homozygous mice lacking the TG1 gene thus suffer from life-threatening malfunctions of the stratum corneum and die quickly after birth (Matsuki et al, Proc. Nat. Acad. Sci. 95, 1998). On the other hand, in humans, mutations carried by TG1 are responsible for more or less serious forms of ichthyosis (Huber et al. Science 267, 1995).

The integrity of the skin barrier and the ability thereof to repair itself change over the course of skin ageing. An overall deficiency in lipids is observed, resulting in a decrease in the lipid multi-layers of the extracellular compartment of the stratum corneum. These functional changes are linked to an increased susceptibility of older skins to external stresses (Ghadially R. et al., J Clin Invest., 1995, 95(5): p. 2281-90).

Changes to the skin barrier may occur during the course of external stresses, independently of intrinsic or photo-induced ageing.

The expression "external stresses" is understood to means stresses which may be produced by the environment. For example, these include stresses such as pollution, UV rays, or irritant products such as surfactants, preservatives or fragrances, and mechanical stresses such as abrasion, shaving or epilation. Pollution is also understood to mean both "external" pollution, caused for example by diesel particles, ozone, or heavy metals, and "internal" pollution, which may be caused in particular by the emissions of solvents of paints, glues, or wallpapers (such as toluene, styrene, xylene or benzaldehyde), or by the smoking of cigarettes. The dryness of the atmosphere is also a significant cause of skin stress. These external stresses lead to a change in barrier function, which translates into skin discomfort, unpleasant feelings such as tugging or itching, and even excessive weaknesses and reddening.

The people particularly affected by this change to barrier function as a result of external stresses are people said to have "fragile" or "sensitive" skin, that is to say skin which is particularly sensitive to variations in temperature or humidity and/or which reacts particularly dramatically to aggressive products (as in the case of babies' skin for example). In particular, people said to have "fragile" skin include people in which the lipids protecting the stratum corneum become scarce, as is the case in elderly and very elderly individuals (at least 75 years of age) and people in which the composition of the lipids protecting the stratum corneum is modified, as is the case in diabetic individuals, dialysis patients, or those affected by certain illnesses. People said to have "sensitive" skin have a reduced threshold of reactivity, which may be linked to neurogenic hyperactivity. These sensitive skins will present clinical signs much more quickly and frequently than other types of skin.

A change to skin barrier function may become evident in particular by a hydration problem, by a loss of skin suppleness, by a change to the radiance of complexion, by the appearance of rough patches over the skin, and more generally by the appearance of signs of skin ageing.

It is therefore necessary to try to prevent these changes or to re-establish the barrier function of the epidermis. The key role of transglutaminase has made it a prime target for reinforcing the barrier function of the epidermis. In the field of cosmetics, the activation of transglutaminase has already been described with the aim of improving barrier function by use of vegetable extracts, for example extracts of *Asiasarum heterotropoides* F., or *Asiasarum sieboldi* F., and of *Apocynum venetum* L, as cited in patent application JP2004115451. Patent application US2007134172 describes the use of flavonoids, preferably extracted from Sidastrum, to obtain batter resistance of the skin to environmental factors, and in particular to drying The inventors have now demonstrated cosmetic and therapeutic activity, in particular dermatological activity, of peptides of general formula (I):

In particular, it has been demonstrated that these peptides, when applied to the skin, reinforce the barrier function of the epidermis and stimulate epidermal regeneration and differentiation. Consequently, the present invention relates to peptides of general formula (I) and to their use in cosmetic or pharmaceutical compositions, as an active ingredient which activates human transglutaminase, to protect the skin and skin appendages against external stresses and to combat the signs of skin ageing.

"Peptide or active ingredient which activates transglutaminase or is capable of activating human transglutaminase" is understood to mean any peptide of general formula (I) capable of increasing the activity of transglutaminase by increasing protein synthesis of transglutaminase (by direct or indirect modulation of gene expression of transglutaminase), by increasing enzyme activity of transglutaminase, or by other biological processes, such as stabilisation of the transglutaminase protein or stabilisation of RNA messenger transcripts.

Skin is understood to mean all the covering tissues forming the skin and mucous membranes.

In accordance with the invention, the term "skin appendages" includes all the keratin appendages present on the surface of the body, in particular body hairs, eyelashes, eyebrows, nails and head hair.

"Topical application" means the application or spreading of the active ingredient according to the invention, or of a composition containing it, to or over the surface of the skin.

"Physiologically suitable" means that the active ingredient according to the invention, or a composition containing it, is suitable for skin contact without any toxic reactions or intolerance being provoked.

The invention therefore firstly relates to a peptide having a sequence according to general formula (I):

in which
X$_1$ is alanine, valine or any amino acid,
X$_2$ is alanine, valine or any amino acid,
X$_3$ is glutamine or asparagine,
X$_4$ is proline, valine or any amino acid,
AA is any amino acid, or a derivative thereof, and n and p are integers between 0 and 4,
R$_1$ is the primary amine function of the N-terminal amino acid, either free or substituted with a group of the acyl type having a saturated or unsaturated C$_1$ to C$_{30}$ alkyl chain selected from an acetyl group or an aromatic group. The aromatic group substituting the primary amine function may be selected from a group of the benzoyl, tosyl or benzyloxycarbonyl type.
R$_2$ is the hydroxyl group of the carboxyl function of the C-terminal amino acid, either free or substituted with a group selected from a C$_1$ to C$_{30}$ alkyl chain or an NH$_2$, NHY or NYY group where Y represents a C$_1$ to C$_4$ alkyl chain.

Said sequence of general formula (I) being formed of 4 to 15 amino acid residues.

Said sequence of general formula (I) possibly including derivatives or substitutions of amino acids AA, X$_1$, X$_2$, X$_3$ or X$_4$ with other chemically equivalent amino acids.

According to a particularly preferred embodiment of the invention, the peptide has the following sequence:

```
                                    (SEQ ID NO: 1)
Val-Val-Arg-Arg-Gly-Gln-Pro-Phe-Trp-Leu (SEQ ID NO: 2)
Val-Ala-Arg-Arg-Gly-Gln-Pro-Phe-NH2

(SEQ ID NO: 3)
Ala-Ala-Arg-Arg-Gly-Asn-Pro (SEQ ID NO: 4)
Arg-Arg-Gly-Gln (SEQ ID NO: 5)
Arg-Arg-Gly-Gln-NH2

(SEQ ID NO: 6)
Ala-Ala-Arg-Arg-Gly-Asn (SEQ ID NO: 7)
Val-Val-Arg-Arg-Gly-Gln-NH2

(SEQ ID NO: 8)
Ala-Val-Arg-Arg-Gly-Asn
```

According to a particularly advantageous embodiment, the peptide corresponds to sequence SEQ ID NO: 5.

The amino acids forming the peptide according to the invention and called AA or X may have isomeric configuration L- and D-. The amino acids are preferably in the L form.

Amino acid derivative means an amino acid having a chemically modified side chain.

The invention also relates to homologous forms of these sequences. According to the invention, the term "homologous" means any peptide sequence which is at least 80% identical, preferably at least 90% identical to said peptide sequence selected from sequences SEQ ID NO: 1 to SEQ ID NO: 8. "Peptide sequence which is at least X % identical"

means a percentage of identity between the amino acid residues of the two sequences to be compared obtained after optimal alignment of the two sequences. Optimal alignment is obtained by means of local homology algorithms, such as those used by computer software programs BLAST P or T BLAST N available on the NCBI website.

The term "homologous" may also denote a peptide which differs from the sequence of a peptide of sequence SEQ ID NO: 1 to SEQ ID NO: 8 by the substitution of chemically equivalent amino acids, that is to say by the substitution of a residue with another having the same characteristics. Conventional substitutions are thus made between Ala, Val, Leu and Ile; between Ser and Thr; between the acid residues Asp and Glu, between Asn and Gln, and between the base residues Lys and Arg, or between the aromatic residues Phe and Tyr.

"Peptide" means the natural or synthetic peptide of the invention as described above, or at least one of the fragments thereof, or at least one of the derivatives thereof, whether obtained by proteolysis or in a synthetic manner, or any natural or synthetic peptide of which the sequence is formed completely or in part by the sequence of the peptide described above. In particular, the derivatives of peptides are the amino acids and the peptides interconnected by a pseudo-peptide bond. "Pseudo-peptide bond" means any type of bond able to replace "conventional" peptide bonds.

So as to improve the resistance to degradation, it may be necessary to use a protected form of the peptide according to the invention. The form of protection must obviously be a biologically compatible form and must be compatible with a use in the field of cosmetics or of pharmacy. A substitution with an $R_1$ group of the acyl type having a saturated or unsaturated $C_1$ to $C_{30}$ alkyl chain selected from an acetyl group or an aromatic group is preferably used to protect the primary amine function of the N-terminal amino acid. A substitution with an $R_2$ group of the $C_1$ to $C_{30}$ alkyl chain type, or an $NH_2$, NHY or NYY group where Y is $C_1$ to $C_4$ alkyl chain is preferably used to protect the carboxyl function of the C-terminal amino acid.

The peptide according to the invention can be protected at the N-terminal or C-terminal end, or at both ends.

The invention thus relates to a composition as defined above, characterised by the fact that the peptide of sequence SEQ ID NO: 1 to SEQ ID NO: 8 is in protected or unprotected form.

The peptide of general formula (I) according to the invention can be obtained from constitutive amino acids or derivatives thereof, either by conventional chemical synthesis (in solid phase or in homogeneous liquid phase) or by enzymatical synthesis (Kullman et al., J. Biol. Chem. 1980, 225, 8234).

The peptide according to the invention may be of natural or synthetic origin, According to the invention, the peptide is preferably obtained by chemical synthesis.

According to the invention, the active ingredient may be a single peptide, a mixture of peptides or of peptide derivatives and/or of peptides formed of amino acid derivatives.

According to the invention, said peptide or mixture of peptides may be used as a pharmaceutical composition.

According to an advantageous embodiment of the invention, the peptide according to the invention is solubilised in one or more physiologically suitable solvents used conventionally by a person skilled in the art, such as water, glycerin, ethanol, propanediol, propylene glycol, butylene glycol, dipropylene glycol, ethoxylated or propoxylated diglycols, cyclic polyols, or any other mixture of these solvents.

According to another advantageous embodiment of the invention, the peptide according to the invention is solubilised in a cosmetic or pharmaceutical vector such as liposomes, or adsorbed on powdery organic polymers, mineral supports such as talcs and bentonites, and are more generally solubilised in, or fixed on, any physiologically suitable vector.

The invention secondly relates to a cosmetic or pharmaceutical composition, in particular a dermatological composition, containing, in a physiologically suitable medium, a peptide of general formula (I) as an active ingredient which is able to activate human transglutaminase. According to a particularly advantageous embodiment of the invention, the peptide is used alone or in combination with at least one other active ingredient.

It is clear that the invention relates to mammals in general, more particularly to human beings.

The peptide according to the invention is more specifically preferably able to activate human transglutaminases of type 1, 2a, 2b, 3 or 5.

According to an advantageous embodiment of the invention, the active ingredient according to the invention is present in the compositions of the invention at a concentration between approximately 0.0005 and 500 ppm (parts per million), and preferably at a concentration between approximately 0.01 and 5 ppm, based on the total weight of the end composition.

This range of concentrations represents the effective amount of active ingredient corresponding to the amount necessary to obtain the desired result, that is to say to activate transglutaminase with the aim of reinforcing the skin barrier function and of stimulating epidermal regeneration and differentiation.

The composition according to the invention is preferably present in a form suitable for topical application and comprising a medium which is physiologically suitable for the skin and skin appendages. "Physiologically suitable" means media which are suitable for use in contact with human skin or skin appendages, with no risk of toxicity, incompatibility, instability, allergic reaction and other side effects.

The compositions intended for application on the skin and skin appendages may be present in the form of aqueous or hydro-alcohol solution, water-in-oil or oil-in-water emulsion, microemulsion, aqueous or anhydrous gel, serum, vesicle dispersion, patch, cream, spray, salve, ointment, lotion, colloid, solution, suspension, etc.

The composition which can be used according to the invention may consist, in particular, of a hair care composition, in particular a shampoo, a conditioner, a cleansing lotion, a hair cream or hair gel, a restructuring lotion for hair, a mask, etc. The cosmetic composition according to the invention may be used in particular in treatments involving application which may, or may not, be followed by rinsing, or in the form of a shampoo. The compositions can also be applied to the skin appendages in the form of a dye or mascara to be applied by brush or comb, in particular to the eyelashes, eyebrows or hair, or in the form of nail care such as varnishes.

It is understood that the active ingredient according to the invention can be used alone or in combination with at least one other active ingredient in a cosmetic composition, or for the preparation of a pharmaceutical and/or dermatological composition. The compositions which can be used according to the invention advantageously also contain various protective or anti-ageing active ingredients intended, in particular, to prevent and/or treat disorders linked to ageing.

The following classes of ingredients are included by way of non-limiting example: other active peptide agents, vegetable extracts, healing agents, anti-ageing agents, anti-wrinkle agents, soothing agents, anti-radical agents, anti-UV agents, agents stimulating synthesis of dermal macromolecules or energy metabolism, hydrating agents, anti-bacterial agents, anti-fungal agents, anti-inflammatory agents, anaesthetic agents, agents modulating skin differentiation, pigmentation or depigmentation, agents stimulating nail growth or hair growth, etc. An anti-radical or antioxidant agent, or an agent stimulating synthesis of dermal macromolecules, or an agent stimulating energy metabolism is preferably used.

In addition, additives such as thickening agents, emulsifiers, moistening agents, emollients, fragrances, antioxidants, filmogenic agents, chelating agents, sequestering agents, conditioning agents, etc. can be added to the composition.

The compositions according to the invention can be applied by any suitable method, for example orally, parenterally or by external topical application, and their formulation will be adapted by a person skilled in the art, in particular for cosmetic or dermatological compositions. The compositions according to the invention are advantageously intended for topical skin application. These compositions must therefore contain a physiologically suitable medium, that is to say one which is compatible with the skin and skin appendages, and include all cosmetic or dermatological forms. In particular, these compositions can be in the form of creams, oil-in-water or water-in-oil emulsions or multiple emulsions, solutions, suspensions, gels, milks, lotions, sticks or powders, and are suitable for application on the skin, lips and/or skin appendages. These compositions contain the excipients necessary for their formulation, such as solvents, thickening agents, diluents, surfactants, antioxidants, colorants, preservatives and fragrances.

According to another form of the invention, the compositions will be suitable for oral administration for pharmaceutical use. The compositions may therefore be present in particular in the form of pills, capsules, gel capsules, chewing pastilles, powders to be consumed as such or to be mixed extemporaneously with a liquid, syrups, gels, and any other form known to a person skilled in the art. They will contain excipients of suitable formulation, such as colorants, sweeteners, flavourings, fillers, binders and preservatives.

In particular, these compositions can be present in the form of an aqueous, hydro-alcohol or oily solution; an oil-in-water or water-in-oil emulsion or multiple emulsions; they can also be present in the form of creams, suspensions, or powders suitable for application to the skin, mucous membranes, lips and/or skin appendages. These compositions may also be more or less fluid and may look like a cream, lotion, milk, serum, ointment, gel, paste or mousse. They may also be present in solid form, such as a stick, or may be applied to the skin in the form of an aerosol. The can be used as a care product and/or as a make-up product for the skin.

These composition also contain any additive commonly used in the intended field of application as well as the additives necessary for the formulation of said compositions, such as solvents, thickening agents, diluents, antioxidants, colorants, sunscreens, self-tanning agents, pigments, fillers, preservatives, fragrances, odour absorbers, cosmetic or pharmaceutical ingredients, essential oils, vitamins, essential fatty acids, surfactants, filmogenic polymers, etc.

In any case, a person skilled in that art will ensure that these additives and their proportions are selected so as not to be detrimental to the advantageous properties sought of the composition according to the invention. For example, these additives may correspond to 0.01 to 20% of the total weight of the composition. When the composition of the invention is an emulsion, the fatty phase may be 5 to 80% by weight, and preferably from 5 to 50% by weight based on the total weight of the composition. The emulsifiers and co-emulsifiers used in the composition will be selected from those used conventionally within the field in question. For example, they can be used in a proportion in the range of 0.3 to 30% by weight, based on the total weight of the composition.

The invention thirdly relates to the use of a cosmetic composition containing the peptide of general formula (I) as an active ingredient to reinforce the skin barrier function and to stimulate epidermal regeneration and differentiation.

"Reinforce the skin barrier function and stimulate epidermal regeneration and differentiation" means an improvement to the structure of the cornified layer, an increase in the signs of cellular regeneration such as the density of the basal epidermal layers and the speed of migration of fibroblasts, and an increase in the expression of markers of keratinocyte differentiation.

The invention fourthly relates to the use of a cosmetic composition containing the peptide of general formula (I) as an active ingredient to combat in a preventative and/or curative manner, the signs of skin ageing, and more particularly photo-induced ageing (photo-ageing). Signs of skin ageing means any changes to the external appearance of the skin and skin appendages caused by ageing, such as superficial rough patches on the cornified layer, fine lines and wrinkles, and also any internal change to the skin which is not systematically translated into a modified external appearance, such as thinning of the dermis or any other internal degradation of the skin following exposure to ultraviolet (UV) rays.

The invention fifthly relates to the use of a cosmetic composition containing the peptide of general formula (I) as an active ingredient to protect the skin and skin appendages against any type of external stress.

In particular, the invention relates to the use of a cosmetic composition containing an effective amount of peptide according to the invention to prevent or treat the damage caused to the skin and skin appendages by mechanical treatments, such as shaving or epilation.

In particular, the invention relates to the use of a cosmetic composition containing an effective amount of peptide according to the invention to prevent or treat the damage caused to the skin and skin appendages by extreme climatic conditions or extreme variations in temperature and hygrometry.

In particular, the invention relates to the use of a cosmetic composition containing an effective amount of peptide according to the invention to prevent or treat the damage caused to the skin and skin appendages by exposure to ultraviolet (UV) rays.

The invention sixthly relates to a cosmetic treatment method characterised in that a composition containing an effective amount of active ingredient is applied topically to the skin or skin appendages to prevent or treat the signs of skin ageing or to protect the skin and skin appendages against external stresses.

In particular, the invention relates to a cosmetic treatment method to protect the skin and skin appendages against stresses caused by UV rays.

Lastly, the invention relates to the use of the peptide of general formula (I) to prepare a pharmaceutical composition to prevent or treat pathologies characterised by a change to the barrier function, such as hypersensitive, irritated or reactive skin, and atopic eczema.

Specific embodiments of this cosmetic treatment method are also clear from the description above. Further advantages and features of the invention will become clearer upon reading the non-limiting examples below, provided merely by way of illustration.

LIST OF FIGURES

FIG. 1: Graph showing the assay results of total transglutaminase activity in normal human keratinocytes treated with 1% peptide SEQ ID NO: 5.

Example 1

Demonstration of the Increase in Total Enzyme Activity of Transglutaminases by Peptide SEQ ID NO: 5

The objective of this study was to determine the influence of peptide SEQ ID NO: 5 on the total activity of transglutaminases in normal human keratinocytes (NHKs). To this end, the total enzyme activity of transglutaminases was assayed by spectrophotometry by means of an amino acid donor substrate, the amino acids being labelled with fluorescein.

Protocol:

NHKs were placed in black 96-well plates. After four days of culture, the NHKs were treated with a 1% solution of a mother solution containing 50 ppm of peptide SEQ ID NO: 5 for 24 or 48 hours (the active ingredient was added every 24 hours). A positive control was created by treating the cells with EGCG (epigallocatechin gallate, the main polyphenol ingredient in green tea) at a concentration of 20 µg/ml. The substrate used was cadaverine labelled with fluorescein (Invitrogen A10466) diluted to 100 µM in the culture medium. The substrate was incubated for two hours with the cells in an amount of 200 µwell). The cells were then rinsed twice in a HBSS buffer and fixed by an ethanoic acid-ethanol-water mixture (1:49:50) for 20 min. After two rinses in ethanol, then three rinses in the HBSS buffer, 100 µl of PBS were added to each well and a reading was taken by spectrophotometer at excitation wavelengths of 485 nm and emission wavelengths of 530 nm. Under these conditions, the transglutaminase activity was proportional to the amount of fluorescence emitted (expressed in fluorescence units), based on the total amount of proteins present in each well, previously assayed by the BCA technique.

Results:

The results are expressed in percent compared to the untreated control and are presented in FIG. 1. Enzyme activity is increased by 30% after 24 hours and by 47.7% after 48 hours in the presence of 0.5 ppm of peptide SEQ ID NO: 5.

Conclusion:

Peptide SEQ ID NO: 5 significantly increases the total enzyme activity of transglutaminases in normal human keratinocytes.

Example 2

Demonstration of the Activating Effect of Peptide SEQ ID NO: 5 on the Expression of TG1, TG2, TG3 and TG5

The objective of this study was to determine the influence of peptide SEQ ID NO: 5 on the expression of the different transglutaminases expressed in the human skin. To this end, a culture of normal human keratinocytes (NHKs) and a skin biopsy were subjected to specific labellings by immunofluorescence. Cultures of normal human fibroblasts were also labelled by immunofluorescence, specifically for TG2, which is expressed in these types of cell.

Protocol of the Immunolabellings of Cultured Normal Human Keratinocytes:

Cultured NHKs were treated with a 1% solution of a mother solution containing 50 ppm of peptide SEQ ID NO: 5 for 24 hours. For immunolabelling by the anti-TG1 antibody, the cells were washed and fixed with 3.7% paraformaldehyde for 10 minutes. The cells were then incubated in the presence of a specific anti-TG1 antibody (Clinisciences BT-621, mouse monoclonal), then in the presence of a suitable secondary antibody coupled to a fluorescent marker. For the other immunolabellings, the cells were washed and fixed with cold methanol for 1 minute. The cells were then incubated in the presence of a specific antibody; anti-TG2 (ABCAM® ab2972 antibody, rabbit polyclonal), anti-TG3 (ABCAM® ab53236 antibody, mouse monoclonal) or anti-TG5 (ABCAM® ab26992 antibody, rabbit polyclonal). After mounting in a medium ad hoc, the slides were observed under epifluorescence microscope (ECLIPSE® E 80i microscope by Nikon Corporation).

Protocol of Immunolabellings of Cultured Normal Human Fibroblasts:

Human dermal fibroblasts were treated and immunolabelled by means of an anti-TG2 antibody by the same protocol as that for the NHKs.

Protocol of Immunolabellings of Skin Biopsies:

Biopsies of human skin were placed in culture at the air/liquid interface. A 1% solution of a mother solution containing 50 ppm of peptide SEQ ID NO: 5 was applied topically over 24 hours.

For the labellings of TG1 and TG2, the skin biopsies were then enclosed in resin and frozen in nitrogen. Sections of approximately 6 µm were then made by cryostat. Immunolabelling was carried out by means of a specific antibody; anti-TG1 (Clinisciences BT-621, mouse monoclonal) or anti-TG2 (ABCAM® ab2972 antibody, rabbit polyclonal), then by means of a suitable secondary antibody coupled to a fluorescent marker. The skin sections were then examined under epifluorescence microscope (ECLIPSE® E 80i microscope by Nikon Corporation).

For the labellings of TG3, the skin biopsies were enclosed in paraffin and histological sections 3 µm thick were made. The slides were deparaffined, hydrated, then immunolabelled by an antibody directed against TG3 (ABCAM® ab53236 antibody, mouse monoclonal), then by a suitable secondary antibody coupled to a fluorescent marker. The skin sections were then examined under epifluorescence microscope (ECLIPSE® E 80i microscope by Nikon Corporation).

Results:

Under all tested conditions, more intense fluorescence was observed in the cultures and in the sections of skin treated with 0.5 ppm of peptide SEQ ID NO: 5 than under untreated, control conditions.

Conclusions:

Peptide SEQ ID NO: 5 (0.5 ppm) stimulates the expression of TG1, TG2, TG3 and TG5 in cultured normal human keratinocytes and also stimulates the expression of TG2 in human fibroblasts.

Peptide SEQ ID NO: 5 (0.5 ppm) stimulates the expression of TG1, TG2 and TG3 in cultivated ex vivo skin biopsies.

Example 3

Demonstration of the Activating Effect of Peptide SEQ ID NO: 5 on Epidermal Differentiation The objective of this study was to determine the influence of peptide SEQ ID NO: 5 on epidermal differentiation. To this end, the expression of the main markers of epidermal differentiation, expressed specifically in the keratinocytes in the suprabasal layers, were studied. The tested markers are transglutaminase 1, pankeratins, filaggrin, involucrin and loricrin. On the other hand, filaggrin, involucrin and loricrin are precursors of the cornified envelope and of transglutaminase substrates.

Protocol of Immunolabellings on Cultured Normal Human Keratinocytes:

Cultured NHKs were treated with a 1% solution of a mother solution containing 50 ppm of peptide SEQ ID NO: 5 for 24 hours. The cells were then washed and fixed with 3.7% paraformaldehyde for 10 minutes. After unmasking of specific sites, the cells were incubated in the presence of a specific antibody directed against TG1 (Clinisciences BT-621, mouse monoclonal), or against loricrin (ABCAM® ab24722 antibody, rabbit polyclonal), or involucrin (NOVOCASTRA® NCL-INV antibody, mouse monoclonal, clone SY5), then incubated in the presence of a suitable secondary antibody coupled to a fluorescent marker. For easier observation, the rings of the cells can be counter-stained by DAPI (4',6' di amidine-2-phenyl indole), a blue fluorescent molecule capable of binding strongly to DNA). After mounting in a medium ad hoc, the slides were observed under epifluorescence microscope (ECLIPSE® E 80i microscope by Nikon Corporation).

Protocol of Immunolabellings on Skin Biopsies:

Biopsies of human skin were placed in culture at the air/liquid interface. A 1% solution of a mother solution containing 50 ppm of peptide SEQ ID NO: 5 was applied topically over 24 hours. The biopsies were then enclosed in paraffin and histological sections 3 µm thick were made. The slides were deparaffined, hydrated, then immunolabelled by an antibody directed against TG1 (Clinisciences BT-621, mouse monoclonal) or cyto-pankeratins (NOVOCASTRA® NCL-CK10 antibody, mouse monoclonal), or loricrin (ABCAM® ab24722 antibody, rabbit polyclonal), or involucrin (NOVOCASTRA® NCL-INV antibody, clone SY5, mouse monoclonal) or filaggrin (Tebu Santa Cruz sc-58761, mouse monoclonal). For easier observation, the rings of the cells can be counter-stained by DAPI (4',6' di amidine-2-phenyl indole, a blue fluorescent molecule capable of binding strongly to DNA). A suitable secondary antibody coupled to a fluorescent marker was then used. After mounting in a medium ad hoc, the slides were observed under epifluorescence microscope (ECLIPSE® E 80i microscope by Nikon Corporation).

Protocol of Immunoblots:

Cultured NHKs were treated with a 1% solution of a mother solution containing 50 ppm of peptide SEQ ID NO: 5 for 24 hours. The cells were then rinsed and detached from the support by scraping in a RIPA buffer in the presence of a cocktail of protease inhibitors (Thermo Scientific, Rockford, USA). The lysed cells were centrifuged at 4° C. at 10,000 rpm for 20 minutes and the supernatants were collected. The samples were then standardised by assaying of the proteins by BCA kit (Pierce, France). The samples were mixed, then subjected to electrophoresis on NUPAGE® 3-8% tris-acetate gel in a NuPAGE NUPAGE® tris-acetate migration buffer, then blotted on a membrane of nitrocellulose by means of a blotting device (Invitrogen, Paisley, UK). The membranes were saturated in 5 TBS milk for 2 hours at ambient temperature, then incubated at 4° C. overnight with a primary antibody directed against TG1 (Clinisciences BT-621, monoclonal mouse) or against involucrin (NOVOCASTRA®NCL-INV antibody, clone SY5, mouse monoclonal) or against loricrin (ABCAM® ab24722 antibody, rabbit polyclonal). After washing by 0.05% TBS-Tween buffer, the membrane was incubated with a suitable secondary antibody coupled to peroxidase. The blots were then developed by means of a chemiluminescent substrate (SuperSignal West Dura Extended Duration Substrate, Pierce, Brebiere, France). The specific bands of proteins thus revealed were quantified by means of a Chemi-Imager technology image analyser (Alpha Innotech Corporation)

Results:

Under all conditions tested by immunofluorescence, more intense fluorescence was observed in the cultures and in the sections of skin treated with 0.5 ppm of peptide SEQ ID NO: 5 than under untreated, control conditions. Epidermal differentiation with the presence of a thicker cornified layer was observed in skin sections ex vivo. Quantitative analysis of the immunoblots made it possible to evaluate the increase in expression of the tested markers. The increase in TG1 was 20%, the increase in involucrin was 30%, and the increase in loricrin was 16%.

Conclusions:

Peptide SEQ ID NO: 5 stimulates the expression of pankeratins, involucrin, filaggrin, loricrin, and TG1 in normal human keratinocytes. Peptide SEQ ID NO: 5 (0.5 ppm) also improves epidermal differentiation and, in particular, morphology of the cornified layer.

Example 4

Demonstration of the Protective Effect of Peptide SEQ ID NO: 5 Against External Stresses The objective of this study was to determine the protective effect on skin of the peptide according to the invention against external stresses. To this end, an ex vivo model of severe stress of the skin barrier was used.

Protocol:

Biopsies of human skin were subjected to stress caused by successive tearing of strata of the cornified layer by means of adhesive tape (technique known as "tape stripping"). The tearing step was repeated 20 times in succession in the same zone. The "stripped" biopsies of human skin were then placed in culture and treated by 0.5 ppm and 1.5 ppm of peptide SEQ ID NO: 5 by the protocol of Example 2 for 48 hours. The skin biopsies were then enclosed in paraffin and histological sections measuring 3 µm thick were made. The sections were deposited on Superfrost Plus slides (Menzel Glaser, Thermo Scientific), then deparaffined in xylene and rehydrated in a series of alcohol-water solutions. The sections were then stained by 50% haematoxylin for 3 minutes, rinsed, then stained with 60% eosin for 3 minutes and rinsed in water. The sections were dehydrated, mounted in Eukitt and examined by optical microscopy.

Results:

The histological sections of skin treated with 0.5 ppm and 1.5 ppm of peptide SEQ ID reveal greater neo-synthesis of the cornified layers. All the epidermal layers demonstrate less vacuolated cells and greater cellular density.

Conclusion:

Peptide SEQ ID NO: 5 improves the reconstruction of the stressed epidermis.

Example 5

Demonstration of the Regenerative Effect of Peptide SEQ ID NO: 5

The objective of this study was to determine the regenerative effect of peptide SEQ ID NO: 5 on dermal fibroblasts and on the epidermis.

Protocol for Use of the In Vitro Ibidi Model of Fibroblast Regeneration:

The Ibidi in vitro healing model was used (Biovalley, Marne la Vallée, France). Human fibroblasts were sown in two separate compartments of an Ibidi insert, which was then placed in a culture dish. On confluence, the insert was removed, thus creating an acellular zone measuring 400 μm wide between the two cellular lawns. The peptide diluted to 1% and 3% from a mother solution containing 50 ppm of peptide SEQ ID NO: 5 was then added to the culture medium, and the treatment was carried out for 48 hours with renewal of the active ingredient every 24 hours. Inspection by phase contrast microscopy (Olympus CK40 microscope, ×5, connected to an Olympus E-510 camera) was carried out at different times (0 to 48 hours) during the migration process.

Protocol of the Study of Epidermal Regeneration:

Biopsies of human skin were placed in culture at the air/liquid interface. A 1% solution of a mother solution containing 50 ppm of peptide SEQ ID NO: 5 was applied topically, then the samples were incubated for 24 hours. The skin biopsies were then enclosed in paraffin and histological sections 3 μm thick were made. The sections were deposited on Superfrost Plus slides (Menzel Glaser, Thermo Scientific), then deparaffined in xylene and rehydrated in a series of alcohol-water solutions. The sections were then stained by 50% haematoxylin for 3 minutes, rinsed, then stained with 60% eosin for 3 minutes and rinsed in water. The sections were then dehydrated, mounted in Eukitt and examined by optical microscopy.

Results:

i) Invasion of the acellular zone with fibroblasts is quicker compared to control conditions if the cells are treated with 0.5 ppm and 1.5 ppm of peptide SEQ ID NO: 5. The effect is dose-dependent.

ii) The histological sections of epidermis treated with peptide SEQ ID NO: 5 demonstrate neo-synthesis of the cornified layer, which appears thicker and better hydrated. Greater density of the cells of the basal layer is also observed, these cells appearing better oriented in the vertical axis and more homogeneous.

Conclusions:

Peptide SEQ ID NO: 5 regenerates dermal fibroblasts and the epidermis. It induces greater cohesion of the cornified layers.

Example 6

Preparation of Compositions

1—Sun Protection Cream:

| Commercial names | INCI names | Mass fraction |
|---|---|---|
| PHASE A | | |
| Demineralised water | Aqua (Water) | qsp |
| PEMULEN ™ TR1 | Acrylates/C10-30 Alkyl Acrylate Crosspolymer | 0.40 |
| Glycerin | Glycerin | 3.00 |
| NIPASTAT ® Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| PARSOL ® MCX | Ethylhexyl Methoxycinnamate | 7.50 |
| EUSOLEX ® 4360 | Benzophenone-3 | 3.00 |
| PARSOL ® 1789 | Butyl Methoxydibenzoylmethane | 2.00 |
| MYRITOL ® 318 | Caprylic/Capric Triglyceride | 4.00 |
| EMULGADE ® SEV | Hydrogenated Palm Glycerides (and) Ceteareth-20 (and) Ceteareth-12 (and) Cetearyl Alcohol | 5.00 |
| Propylparaben | Propylparaben | 0.15 |
| NACOL ® 16-98 | Cetyl Alcohol | 1.00 |
| PHASE C | | |
| TEA | Triethanolamine | 0.20 |
| PHASE D | | |
| Peptide SEQ ID NO: 5 | | 3 ppm |
| Parfum | Parfum (Fragrance) | qsp |
| Colorant | | qsp |

The components of phase A and phase B are heated separately between 70° C. and 75° C. Phase B is emulsified in phase A with stirring. Phase C is added at 45° C., increasing stirring. Phase D is then added when the temperature is below 40° C. Cooling is continued to 25° C. with vigorous stirring.

2—Anti-Ageing Cream:

| Commercial names | INCI names | Mass fraction |
|---|---|---|
| Phase A | | |
| MONTANOV ™ 68 | Cetearyl Alcohol (and) Cetearyl Glucoside | 6.00 |
| Squalane | Squalane | 3.00 |
| Cetiol ® SB 45 | Butyrospermum Parkii (Shea Butter) | 2.00 |
| WAGLINOL ™ 250 | Cetearyl Ethylhexanoate | 3.00 |
| AMERCHOL L-101 ™ | Mineral Oil (and) Lanolin Alcohol | 2.00 |
| ABIL ® 350 | Dimethicone | 1.50 |
| BHT | BHT | 0.01 |
| Coenzyme Q10 | Ubiquinone | 0.10 |
| Phase B | | |
| Avocado oil | Persea Gratissima (Avocado) Oil | 1.25 |
| PHENONIP ® | Phenoxyethanol (and) Methylparaben (and) Ethylparaben (and) Butylparaben (and) Propylparaben (and) Isobutylparaben | 0.75 |
| Phase C | | |
| Demineralised water | Aqua (Water) | qsp |
| Butylene Glycol | Butylene Glycol | 2.00 |
| GLUCAM ® E10 | Methyl Gluceth-10 | 1.00 |
| Allantoin | Allantoin | 0.15 |
| CARBOPOL ® Ultrez 10 | Carbomer | 0.20 |
| Phase D | | |
| TEA | Triethanolamine | 0.18 |
| Phase E | | |
| Peptide SEQ ID NO: 5 | | 0.5 ppm |
| GP4G | Water (and) Artemia Extract | 1.50 |
| Collaxyl | Water (and) Butylene Glycol (and) Hexapeptide-9 | 3.00 |
| Phase F | | |
| Fragrance | Parfum (Fragrance) | qsp |
| Colorant | | qsp |

Prepare and melt phase A at 65-70° C. Heat phase C to 65-70° C. Phase B is added to phase A just before emulsifying A in B. At approximately 45° C., the carbomer is neutralised by adding phase D. Phase E is then added with slight stirring, and cooling is continued to 25° C. Phase F is then added if desired.

3—Protective Day Cream:

| Commercial names | INCI Names | Mass fraction |
|---|---|---|
| Phase A | | |
| EMULIUM® Delta | Cetyl alcohol (and) Glyceryl Stearate (and) PEG-75 Stearate (and) Ceteth-20 (and) Steareth-20 | 4.00 |
| LANETTE® O | Cetearyl Alcohol | 1.50 |
| DOW CORNING® 200 Fluid/100cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| CEGESOFT® PS6 | Vegetable Oil | 1.00 |
| Vitamin E | Tocopherol | 0.30 |
| PHENONIP® | Phenoxyethanol (and) Methylparaben (and) Ethylparaben (and) Butylparaben (and) Propylparaben (and) Isobutylparaben | 0.70 |
| Phase B | | |
| Demineralised water | Aqua | qsp 100 |
| Glycerin | Glycerin | 2.00 |
| CARBOPOL® EDT 2020 | Acrylates/C10-30Alkyl Acrylate Crosspolymer | 0.15 |
| KELTROL® BT | Xanthan Gum | 0.30 |
| Phase C | | |
| Sodium Hydroxide (sol. 10%) | Sodium Hydroxide | 0.30 |
| Phase D | | |
| Demineralised water | Aqua | 5.00 |
| STAY-C® 50 | Sodium Ascorbyl Phosphate | 0.50 |
| Phase E | | |
| Butylene Glycol | Butylene Glycol | 2.00 |
| Dekaben CP | Chlorphenesin | 0.20 |
| Phase F | | |
| GP4G | Water (and) Artemia Extract | 1.00 |
| Peptide SEQ ID NO: 5 | | 5 ppm |

Prepare phase A and heat to 75° C. with stirring. Prepare phase B by dispersing the CARBOPOL® EDT 2020 Acrylates/C10-30Alkyl Acrylate Crosspolymer, then the xanthan gum with stirring. Leave to rest. Heat to 75° C.

At temperature, emulsify A in B with rotor-stator stirring. Neutralise with phase C with rapid stirring. After cooling to 40° C., add phase D, then phase E. Cooling is continued with gentle stirring and phase F is added.

Applicants incorporate by reference the material contained in the accompanying computer readable Sequence Listing entitled "US09-130SequenceListing.txt", which was created on Feb. 22, 2012, and is 1,887 bytes in size, and hereby confirm that the information recorded in the computer readable form is identical to the written sequence listing.

The invention claimed is:

1. A method for protecting skin, the method comprising: administering a composition containing a peptide of formula:
(SEQ ID NO: 2) Val-Ala-Arg-Arg-Gly-Gln-Pro-Phe-NH$_2$;
(SEQ ID NO: 5) Arg-Arg-Gly-Gln-NH$_2$; or
(SEQ ID NO: 7) Val-Val-Arg-Arg-Gly-Gln-NH$_2$
to reinforce the barrier function of the epidermis and to stimulate epidermal regeneration and differentiation, wherein administering the composition includes applying the composition before exposure to an external stress acting on the skin.

2. The method of claim 1, wherein the composition comprises an effective amount of the peptide used alone or in combination with at least one other active ingredient.

3. The method of claim 1, wherein the composition includes the peptide solubilized in one or more physiologically suitable solvents selected form the group consisting of water, glycerin, ethanol, propanediol, propylene glycol, butylene glycol, dipropylene glycol, ethoxylated diglycols, propoxylated diglycols, cyclic polyols, and combinations thereof.

4. The method of claim 1, wherein the peptide is present in the composition at a concentration between approximately 0.0005 and 500 ppm.

5. The method of claim 4, wherein said peptide is present at a concentration between approximately 0.01 and 5 ppm.

6. The method of claim 1, wherein administering includes topically applying the composition.

7. The method of claim 2, wherein the other active ingredient includes at least one of an antioxidant active ingredient, an active ingredient stimulating synthesis of dermal macromolecules, and an active ingredient stimulating energy metabolism.

8. The method of claim 1, wherein administering the composition includes applying the composition for activating human transglutaminases of type 1, 2a, 2b, 3 or 5.

9. The method of claim 1, wherein administering the composition includes topically applying the composition to skin before exposure to ultraviolet radiation, shaving or epilation.

* * * * *

SEQUENCE LISTING

```
<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 1

Val Val Arg Arg Gly Gln Pro Phe Trp Leu
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (8)..(8)
<223> OTHER INFORMATION: AMIDATION

<400> SEQUENCE: 2

Val Ala Arg Arg Gly Gln Pro Phe
1               5

<210> SEQ ID NO 3
<211> LENGTH: 7
<212> TYPE: PRT
```

```
<213> ORGANISM: Artificial Sequence
<220> FEATURE:
<223> OTHER INFORMATION: Synthetic Peptide

<400> SEQUENCE: 3

Ala Ala Arg Arg Gly Asn Pro
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 4

Arg Arg Gly Gln
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: AMIDATION

<400> SEQUENCE: 5

Arg Arg Gly Gln
1

<210> SEQ ID NO 6
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 6

Ala Ala Arg Arg Gly Asn
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (6)..(6)
<223> OTHER INFORMATION: AMIDATION

<400> SEQUENCE: 7

Val Val Arg Arg Gly Gln
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide
```

```
<400> SEQUENCE: 8

Ala Val Arg Arg Gly Asn
1               5
```